(12) United States Patent
Connelly et al.

(10) Patent No.: US 7,901,950 B2
(45) Date of Patent: Mar. 8, 2011

(54) METHOD FOR ASSESSING DISEASE STATES BY PROFILE ANALYSIS OF ISOLATED CIRCULATING ENDOTHELIAL CELLS

(75) Inventors: Mark Carle Connelly, Doylestown, PA (US); Gerald V. Doyle, Radnor, PA (US); Galla Chandra Rao, Princeton Junction, NJ (US); Leon W. M. M. Terstappen, Huntingdon Valley, PA (US)

(73) Assignee: Veridex, LLC, Raritan, NJ (US)

( * ) Notice: Subject to any disclaimer, the term of this patent is extended or adjusted under 35 U.S.C. 154(b) by 277 days.

(21) Appl. No.: 11/701,763

(22) Filed: Feb. 2, 2007

(65) Prior Publication Data

US 2007/0154960 A1 Jul. 5, 2007

(51) Int. Cl.
*G01N 33/553* (2006.01)
*G01N 33/00* (2006.01)
*G01N 1/00* (2006.01)
*G01N 1/18* (2006.01)

(52) U.S. Cl. ......... 436/526; 435/7.2; 435/7.24; 435/372; 435/287.2; 436/518; 436/523; 436/536; 436/538; 436/10; 436/17; 436/18; 436/63; 436/172; 436/176; 436/177; 422/73; 422/82.05; 422/101

(58) Field of Classification Search ............... 435/1.1, 435/2, 7.2, 7.23, 7.24, 372, 287.2, 40.51; 436/526, 536, 538, 10, 17, 18, 63, 64, 172, 436/174–177, 518, 523; 422/68.1, 73, 82.05, 422/101

See application file for complete search history.

(56) References Cited

U.S. PATENT DOCUMENTS

| | | | |
|---|---|---|---|
| 3,970,518 A | 7/1976 | Giaever | |
| 4,018,886 A | 4/1977 | Giaever | |
| 4,230,685 A | 10/1980 | Senyei et al. | |
| 4,267,234 A | 5/1981 | Rembaum | |
| 4,452,773 A | 6/1984 | Molday | |
| 4,554,088 A | 11/1985 | Whitehead | |
| 4,659,678 A | 4/1987 | Forrest et al. | |
| 4,795,698 A | 1/1989 | Owen | |
| 5,200,084 A * | 4/1993 | Liberti et al. | 210/695 |
| 5,597,531 A | 1/1997 | Liberti et al. | |
| 5,698,271 A | 12/1997 | Liberti et al. | |
| 5,876,593 A | 3/1999 | Liberti et al. | |
| 5,985,153 A | 11/1999 | Dolan et al. | |
| 6,136,182 A | 10/2000 | Dolan et al. | |
| 6,184,043 B1 | 2/2001 | Fodstad et al. | |
| 6,190,870 B1 * | 2/2001 | Schmitz et al. | 435/7.23 |
| 6,365,362 B1 * | 4/2002 | Terstappen et al. | 435/7.23 |
| 6,645,731 B2 | 11/2003 | Terstappen et al. | |
| 6,861,259 B2 | 3/2005 | Columbus | |
| 6,998,234 B2 | 2/2006 | Fruehauf et al. | |
| 2004/0110241 A1 * | 6/2004 | Segal | 435/7.21 |
| 2005/0244897 A1 * | 11/2005 | Zeiher et al. | 435/7.2 |

FOREIGN PATENT DOCUMENTS

| WO | 2004/045517 A2 | 6/2004 |
|---|---|---|
| WO | 2005/028663 A2 | 3/2005 |

OTHER PUBLICATIONS

U.S. Appl. No. 10/780,349, Rao et al., Aug.18, 2005.
U.S. Appl. No. 09/801,471, Leon W.M.M Terstappen et al., May 30, 2001.
U.S. Appl. No. 10/988,057, Richard L. Columbus, Mar. 24, 2005.
U.S. Appl. No. 10/303,309, Kagan et al., Jun. 27, 2004.
Mutin, M. et al, "Direct Evidence of E ndothelial I njury i n Acute Myoc ardial Infarction an d Unstable Angina b y Demonstration of Circulating Endothelial C ells," Blood, 93:2951-2958, 1999.
Beerepoot, L. et al., "Increased Levels of Viable Circulating Endothelial Cells are an Indicator of Prog ressive Disease i n Canc er Patients," Ann uls o f Oncology, 15:139-145.2004.

* cited by examiner

*Primary Examiner* — Gailene R Gabel

(57) ABSTRACT

Elevated number of Circulating Endothelial Cells (CEC) have been implicated in disease conditions associated with the formation or destruction of blood vessels such as acute coronary syndrome, thrombocytopenic purpura, sickle cell disease, sepsis, lupus, nephrotic syndromes, rejection of organ transplants, surgical trauma and cancer. This invention provides a method for assessing the levels of CEC which vary between different studies using a sensitive enrichment, imaging, and enumeration analysis. CD146 is one of the most specific endothelium-associated cell-surface antigens which can be used in image cytometry. CEC analysis provides an essential tool in prognostic/diagnostic evaluation in the clinic.

6 Claims, 3 Drawing Sheets

METHOD FOR ASSESSING DISEASE STATES BY PROFILE ANALYSIS OF ISOLATED CIRCULATING ENDOTHELIAL CELLS

PRIORITY INFORMATION

This application claims priority to International Application No PCT/US2005/028862, filed 12 Aug. 2005 which claims the benefit to US Provisional Application No. 60/601,585 filed on 12 Aug. 2004.

FIELD OF THE INVENTION

This invention relates to the fields of cardiology, oncology and diagnostic testing. The invention is a useful adjunct in clinical diagnosis and prognosis for diseases such as melanoma, solid tumors, and cardiovascular disorders. The invention is also useful in the screening of therapeutic agents used in cardiovascular disorders, cancer or the like. It is applicable for monitoring stenotic state after surgery or stent implantation. More specifically, the present invention provides reagents and methods that facilitate analysis and enumeration of rare circulating endothelial cells isolated from biological samples, providing a basis for diagnostic and/or prognostic evaluation in clinically relevant diseases.

BACKGROUND OF THE INVENTION

The American Heart Association estimates that approximately 600,000 patients undergo heart bypass surgery and 400,000 have stents implanted to open blocked arteries. Approximately 6 million patients visit the emergency rooms each year because of suspected heart attacks. In each of these situations, the patients may be treated with angiogenesis-stimulating drugs. Thus, critical analysis in assessing the efficacy of these drugs and/or the disease state would provide a valuable tool to the clinician.

Endothelial cells are involved in the formation of blood vessels, or angiogenesis. This process is important for the growth of tumors and as a transport mechanism for circulating tumor cells (CTCs). Anti-angiogenesis drugs are in clinical development, either alone or in combination with traditional chemotherapeutic agents. Analysis of endothelial cells, after enrichment, using CELLTRACKS, a diagnostic imaging system, has applications in clinical trails as a tool to monitor efficacy as well as a tool for monitoring cancer patients receiving these drugs once they are marketed. Further, this type of analysis has applications in monitoring melanoma patients.

Circulating endothelial cells have been implicated in cardiovascular (such as assessing cardiac risk), inflammatory, and infectious diseases. Mature vascular endothelial cells exist in a variety of physiologic states ranging from quiescent to proliferative and activated to dysfunctional to terminal, whereupon they detach from the basement membrane and surrounding endothelial cells and enter the circulation. As the cause, fate and role of circulating endothelial cells (CECs) becomes better understood, the in vitro enumeration and characterization of CECs may offer a unique opportunity to study the vasculature and improve our understanding of a variety of homeostatic and disease processes. For instance, elevation of CECs has been observed in all of the above mentioned pathological conditions i.e. cancer, cardiovascular, inflammatory, infectious, and autoimmune disease (Mutin, M., Canavey, I., Blann, A., Bory, M., Sampol, J., Dignat-George, F. Direct evidence of endothelial injury in acute myocardial infarction and unstable angina by demonstration of circulating endothelial cells. Blood, 93: 2951-2958, 1999; also see WO 2004/045517). In particular, cancer CEC levels may increase due to active tumor angiogenesis, vascular damage as a result of tumor apoptosis/necrosis or as a side effect of therapy on non-tumor vasculature. However, the lack of standardized assay methods, the lack of consensus on the definition of a CEC (Beerepoot, L. V., Mehra, N., Vermaat, J. S. P., Zonnenberg, B. A., Gebbink, M. F. G. B., Voest, E. E. Increased levels of viable circulating endothelial cells are an indicator of progressive disease in cancer patients. Annals of Oncology, 15: 139-145, 2004) and disease heterogeneity have led to a wide variation in the reported ranges of CECs (1 to 5700 per mL). All of these factors make interpretation and comparison of existing studies quite difficult if not impossible.

Surface antigens of vascular endothelial cells has come from several lines of research, including studies of lymphocyte homing, inflammation, blood clotting, and tumor metastasis. Monoclonal antibodies (mAbs) have proven to be valuable tools for dissecting the antigenic structure of endothelial cells in different organs, tissues or segments of the vascular system, and the endothelial responses to inflammation, tissue damage, and tumor growth. Furthermore, mabs have been used in the biochemical and molecular genetic characterization of endothelial antigens and in the functional analyses of endothelial molecules in vitro and in vivo.

Several categories of endothelial antigens have been distinguished, based on their distribution patterns in normal and lesion blood vessels. These include (i) antigens with wide distribution in the vascular system, such as Factor VIII-related antigen; (ii) antigens restricted to vessels in specific organs or tissues, or to unique histologic types of vessels, as illustrated by vascular addressins and GlyCAM-1; and (iii) inducible antigens, such as E-selectin, VCAM-1, and ICAM-1, that are not present or expressed at low levels in normal endothelium but are upregulated in inflamed tissues in vivo and/or induced or cultured endothelial cells by proinflammatory cytokines, notably tumor necrosis factor (TNF) and interleukin-1 (IL-1).

Many laboratory and clinical procedures employ bio-specific affinity reactions for isolating rare cells from biological samples. Such reactions are commonly employed in diagnostic testing, or for the separation of a wide range of target substances, especially biological entities such as cells, proteins, bacteria, viruses, nucleic acid sequences, and the like.

Various methods are available for analyzing or separating target substances based upon complex formation between the substance of interest and another substance to which the target substance specifically binds. Separation of complexes from unbound material may be accomplished gravitationally, e.g. by settling, or, alternatively, by centrifugation of finely divided particles or beads coupled to the target substance. If desired, such particles or beads may be made magnetic to facilitate the bound/free separation step. Magnetic particles are well known in the art, as is their use in immune and other bio-specific affinity reactions. See, for example, U.S. Pat. No. 4,554,088. Generally, any material that facilitates magnetic or gravitational separation may be employed for this purpose. However, it has become clear that magnetic separation means are the method of choice.

Small magnetic particles of the type described above are quite useful in analyses involving bio-specific affinity reactions, as they are conveniently coated with biofunctional polymers (e.g., proteins), provide very high surface areas and give reasonable reaction kinetics. Magnetic particles ranging from 0.7-1.5 microns have been described in the patent literature, including, by way of example, U.S. Pat. Nos. 3,970, 518; 4,018,886; 4,230,685; 4,267,234; 4,452,773; 4,554,088; and 4,659,678. Certain of these particles are disclosed to be useful solid supports for immunological reagents.

High gradient magnetic separation with an external field device employing highly magnetic, low non-specific binding, colloidal magnetic particles is the method of choice for separating a cell subset of interest from a mixed population of eukaryotic cells, particularly if the subset of interest comprises but a small fraction of the entire population. Such materials, because of their diffusive properties, readily find and magnetically label rare events, such as tumor cells in blood. For magnetic separations for tumor cell analysis to be successful, the magnetic particles must be specific for epitopes that are not present on hematopoeitic cells.

In summary, a useful diagnostic test needs to be very sensitive and reliably quantitative. A system that provides a consistent, reliable, and reproducable enumeration of target endothelial cells is needed in diagnostic and prognostic analysis of cardiovascular monitoring. A blood test that detects a single or a few endothelial or fungal cells in less than 30 ml of blood would provide a very sensitive and early detection mechanism in disease assessment.

SUMMARY OF THE INVENTION

The present invention is based on several important discoveries which have significant diagnostic, prognostic, therapeutic, and drug discovery ramifications.

Once rare cells are identified in circulation, it is desirable to further characterize the isolated cells phenotypically and/or genotypically. Thus, particular molecules associated with patient disorders, such as nucleic acid molecules, proteins, or carbohydrates connected to the phenotypic or genotypic characteristics may be analyzed. Specifically, methods are provided for measuring the level of expression of predetermined molecules associated with the disorder or on endothelial cells identified in the circulation to assist the clinician in diagnosing melanoma and assessing the efficacy of chemotherapeutic intervention strategies. The current method determines the frequency of CEC's in 4 ml of blood. Endothelial cell confirmation with this method is defined, in part, as nucleated cells expressing S-endol (CD146) and endoglin (CD105), yet lacking the pan-leukocytet marker CD45. Using CD146 in as the capturing antigen and CD105 in the imaging provides a confirmatory process that significantly reduces the variation and unconfirmed target cell counts (unassigned events), and allows confident diagnostic and/or prognostic evaluation of endothelial cells in a biological sample.

A further embodiment utilizes endothelial cell detection with a melanoma antibody such as M330-FITC or M330-PE on the CELLSPOTTER system, a fluorescent imaging device for single cell analysis, or similar cell imaging systems. This provides a method for diagnostic and prognostic analysis of disease.

DETAILED DESCRIPTION OF THE INVENTION

Figure 1:
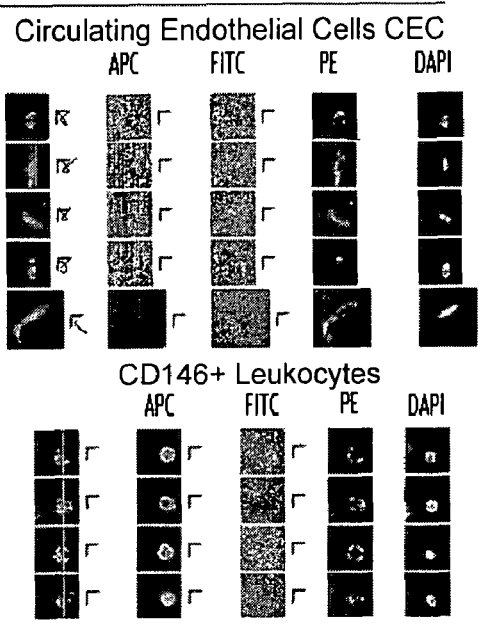
FIG. 1: Endothelial cell capture using CD146 ferrofluid in CELLSPOTTER system, a fluorescent imaging device for single cell analysis.

According to a preferred embodiment, the present invention provides compositions, methods and kits for the rapid and efficient isolation of endothelial cells from biological samples. The methods described may be used effectively to isolate and characterize tumor cells present in a blood sample while at the same time minimizing the selection of non-specifically bound or entrapped cells.

The object of this invention provides for the detection of circulating endothelial cells or fungal cells in assessing disease states or as a tool to monitor the efficacy of drugs. Under the broadest aspect of the invention, there is no limitation on the collection and handling of samples as long as consistency is maintained. Accordingly, the cells can be obtained by methods known in the art.

While any effective mechanism for isolating, enriching, and analyzing CTCs in blood is appropriate, one method for collecting circulating tumor cells combines immunomagnetic enrichment technology, immunofluorescent labeling technology with an appropriate analytical platform after initial blood draw. The associated test has the sensitivity and specificity to detect these rare cells in a sample of whole blood and to investigate their role in the clinical course of the disease in malignant tumors of epithelial origin. From a sample of whole blood, rare cells are detected with a sensitivity and specificity to allow them to be collected and used in the diagnostic assays of the invention, namely predicting the clinical course of disease in malignant tumors.

With this technology, circulating tumor cells (CTC) have been shown to exist in the blood in detectable amounts. This created a tool to investigate the significance of cells of epithelial origin in the peripheral circulation of cancer patients (U.S. Pat. No. 6,365,362 and U.S. Pat. No. 6,645,731).

The CELLSPOTTER System is an automated fluorescence microscopic system for automated enumeration of isolated cells from blood. The system contains an integrated computer controlled fluorescence microscope and automated stage with a magnetic yoke assembly that will hold a disposable sample cartridge. The magnetic yoke is designed to enable ferrofluid-labeled candidate tumor cells within the sample chamber to be magnetically localized to the upper viewing surface of the sample cartridge for microscopic viewing. Software detects cells, labeled with an antibody and having endothelial or fungal origin, from blood.

While isolation of tumor cells for the CELLSPOTTER system, a fluorescent imaging device for single cell analysis, can be accomplished by any means known in the art, one embodiment uses CELLSAVE preservative (U.S. application Ser. No. 10/780,349) for isolating tumor cells using 7.5 ml of whole blood. Cell-specific magnetic particles are added and incubated for 20 minutes. After magnetic separation, the cells bound to the immunomagnetic-linked antibodies are magnetically held at the wall of the tube. Unbound sample is then aspirated and an isotonic solution is added to resuspend the sample. A nucleic acid dye, monoclonal antibodies to the specified marker and CD 45 (a broad-spectrum leukocyte marker) are incubated with the sample. After magnetic separation, the unbound fraction is again aspirated and the bound and labeled cells are resuspended in 0.2 ml of an isotonic solution. The sample is suspended in a cell presentation chamber and placed in a magnetic device whose field orients the magnetically labeled cells for fluorescence microscopic examination in the CELLSPOTTER System. Cells are identified automatically in the CELLSPOTTER System with control cells enumerated by the System and candidate circulating tumor cells presented to the operator for checklist enumeration. An enumeration checklist consists of predetermined morphologic criteria constituting a complete cell (see example 1).

The diagnostic potential of the CELLSPOTTER system, a fluorescent imaging device for single cell analysis, together with the use of intact circulating cells as a prognostic factor, can provide a rapid and sensitive method for determining appropriate treatment. Accordingly in the present invention, the apparatus, method, and kits are provided for the rapid enumeration and characterization of endothelial cells shed into the blood in patients for prognostic assessment.

The methods of the invention are useful in assessing a favorable or unfavorable survival, and even preventing unnecessary therapy that could result in harmful side-effects when the prognosis is favorable. Thus, the present invention can be used for prognosis of any of a wide variety of disorders relating to endothelial enumeration.

The term "biological specimen" includes, without limitation, cell-containing bodily fluids, including without limitation, peripheral blood, tissue homogenates, nipple aspirates, colonic lavage, sputum, bronchial lavage, and any other source of cells that is obtainable from a human subject. An exemplary tissue homogenate may be obtained from the sentinel node in a breast cancer patient.

The term "specific binding pair" as used herein includes antigen-antibody, receptor-hormone, receptor-ligand, agonist-antagonist, lectin-carbohydrate, nucleic acid (RNA or DNA) hybridizing sequences, Fc receptor or mouse IgG-protein A, avidin-biotin, streptavidin-biotin and virus-receptor interactions. "Gene specific probing" refers to methods wherein nucleic acid molecules which are complementary to tumor diathesis associated molecules are used to detect the presence or absence of such molecules. Such nucleic acids may or may not be detectably labeled. Various other determinant-specific binding substance combinations are contemplated for use in practicing the methods of this invention, and will be apparent to those skilled in the art.

The term "antibody" as used herein, includes immunoglobulins, monoclonal or polyclonal antibodies, immunoreactive immunoglobulin fragments such as F(ab), and single chain antibodies (sfV). Also contemplated for use in the invention are peptides, oligonucleotides or a combination thereof which specifically recognize determinants with specificity similar to traditionally generated antibodies. As mentioned previously, complementary nucleic acids are encompassed within the meaning of "specific binding pair". The term "detectably label", is used to herein to refer to any substance whose detection or measurement, either directly or indirectly, by physical or chemical means, is indicative of the presence of the target bioentity in the test sample. Representative examples of useful detectable labels, include, but are not limited to the following: molecules or ions directly or indirectly detectable based on light absorbance, fluorescence, reflectance, light scatter, phosphorescence, or luminescence properties; molecules or ions detectable by their radioactive properties; molecules or ions detectable by their nuclear magnetic resonance or paramagnetic properties. Included among the group of molecules indirectly detectable based on light absorbance or fluorescence, for example, are various enzymes which cause appropriate substrates to convert, e.g., from non-light absorbing to light absorbing molecules, or from non-fluorescent to fluorescent molecules.

The term "enrichment" as used herein refers to the process of substantially increasing the ratio of target bioentities (e.g., tumor cells) to non-target materials in the processed analytical sample compared to the ratio in the original biological sample. In cases where peripheral blood is used as the starting materials, red cells are not counted when assessing the extent of enrichment. Using the method of the present invention, circulating epithelial cells may be enriched relative to leucocytes to the extent of at least 2,500 fold, more preferably 5,000 fold and most preferably 10,000 fold.

Cardiovascular homeostasis is used herein pertains to the maintenance of a biochemical, physiological, or metabolic equilibrium within the heart and blood vessels of a test subject.

Subsets of endothelial cells is used herein pertains to subsets of endothelial cells such as, but not limited to, endothelial progenitor cells.

The preferred magnetic particles for use in carrying out this invention are particles that behave as colloids. Such particles are characterized by their sub-micron particle size, which is generally less than about 200 nm (0.20 microns), and their stability to gravitational separation from solution for extended periods of time. In addition to the many other advantages, this size range makes them essentially invisible to analytical techniques commonly applied to cell analysis. Particles within the range of 90-150 nm and having between 70-90% magnetic mass are contemplated for use in the present invention. Suitable magnetic particles are composed of a crystalline core of superparamagnetic material surrounded by molecules which are bonded, e.g., physically absorbed or covalently attached, to the magnetic core and which confer stabilizing colloidal properties. The coating material should preferably be applied in an amount effective to prevent non-specific interactions between biological macromolecules found in the sample and the magnetic cores. Such biological macromolecules may include carbohydrates such as sialic acid residues on the surface of non-target cells, lectins, glyproteins, and other membrane components. In addition, the material should contain as much magnetic mass per nanoparticle as possible. The size of the magnetic crystals comprising the core is sufficiently small that they do not contain a complete magnetic domain. The size of the nanoparticles is sufficiently small such that their Brownian energy exceeds their magnetic moment. As a consequence, North Pole, South Pole alignment and subsequent mutual attraction/repulsion of these colloidal magnetic particles does not appear to occur even in moderately strong magnetic fields, contributing to their solution stability. Finally, the magnetic particles should be separable in high magnetic gradient external field separators. That characteristic facilitates sample handling and provides economic advantages over the more complicated internal gradient columns loaded with ferromagnetic beads or steel wool. Magnetic particles having the above-described properties can be prepared by modification of base materials described in U.S. Pat. Nos. 4,795,698, 5,597,531 and 5,698,271.

It should be noted that a number of different cell analysis platforms can be used to identify and enumerate endothelial cells in the enriched samples. Examples of such analytical platforms are the CELLSPOTTER system, a magnetic cell immobilization and analysis system, using microscopic detection for manual observation of cells, described in U.S. Pat. Nos. 5,876,593; 5,985,153 and 6,136,182 respectively. All of the aforementioned U.S. Patent Applications are incorporated by reference herein as disclosing the respective apparatus and methods for manual or automated quantitative and qualitative cell analysis. Such devices may be used to advantage in the diagnostic and monitoring kits of the present invention.

Other analysis platforms include laser scanning Cytometry (Compucyte), bright field base image analysis (Chromavision), and capillary Volumetry (Biometric Imaging).

The enumeration of circulating endothelial cells in blood using the methods and compositions of a preferred embodiment of the present invention is achieved by immunomagnetic selection (enrichment) of cells from blood followed by the analysis of the samples by multiparameter flowcytometry. The immunomagnetic sample preparation is important for reducing sample volume and obtaining a $10^4$ fold enrichment of the target (endothelial or fungal) cells. The reagents used for the multiparameter flowcytometric analysis are optimized such that cells are located in a unique position in the multi-dimensional space created by the listmode acquisition of two light scatter and three fluorescence parameters. These include 1) an antibody against the pan-leukocyte antigen, CD45 to identify leucocytes (non-target cells);

2) a cell type specific or nucleic acid dye which allows exclusion of residual red blood cells, platelets and other non-nucleated events; and 3) a biospecific reagent or antibody directed against the target cytostructure or an antibody having specificity for the targets membrane which differs from that used to immunomagnetically select the cells.

It will be recognized by those skilled in the art that the method of analysis of the enriched cell population will depend on the intended use of the invention. For example, in screening for cancers or monitoring for recurrence of disease, as described hereinbelow, the numbers of circulating endothelial cells can be very low. Since there is some "normal" level of endothelial cells, (very likely introduced during venipuncture), a method of analysis that identifies endothelial cells as normal or other target cells is desirable. Microscopy based analyses may prove to be the most accurate. Such examination might also include examination of morphology, identification of known molecules (e.g., oncogenes). Suitable molecules that may be further analyzed in accordance with the methods of the invention are provided.

Alternatively, in disease states wherein the number of circulating target cells far exceeds that observed in the normal population, an analytical method that enumerates such cells should be sufficient. The determination of patient status according to the methods described herein is made based on a statistical average of the number of circulating rare cells present in the normal population. Levels of circulating cells in the early stages patient disease and in patients with later stages can also be statistically determined as set forth herein.

EXAMPLE 1

Semi-Automated Sample Preparation and Analysis for Identification of Circulating Tumor Cells A semi-automated system was developed that processes and analyzes 7.5 ml of blood for the presence of epithelial derived tumor cells. Cells of epithelial cell origin are immunomagnetically labeled and separated from blood. The magnetically captured cells are differentially fluorescent labeled and placed in an analysis chamber. Four-color fluorescent imaging is used to differentiate between debris, hematopoeitic cells and circulating tumor cells (CTC) of epithelial origin. An algorithm is applied on the captured images to enumerate an internal control and identify all objects that potentially classify as tumor cell based on size and immunophenotype. Thumbnail images of each object are presented in a user interface from which the user can determine the presence of tumor cells. In processing the blood of normal donors the internal control showed consistent and reproducible results between systems and operators. CTC were detected in blood samples of patients with metastatic breast cancer, however, other diseases may be analyzed with the system.

To monitor the accuracy of the procedure, a known number of internal control cells are added to the blood before processing. Internal control cells are the subject of U.S. patent application Ser. No. 09/801,471, the entire disclosure of which is incorporated by reference herein. These control cells can be successfully derived from the cancer tumor cell-lines. As described herein, cells from the breast cancer line, SKBR-3, are stabilized and uniquely labeled with the fluorescent membrane dye DiOC16 to permit differentiation from endogenous tumor cells. Approximately 1000 control cells are spiked into each specimen. The control cells express EpCAM and are captured concurrently with the tumor cells. Control cells also express intracellular cytokeratin and staining with CK-PE verifies the quality of this reagent. The percent recovery of added control cells provides an indicator of total reagents and system performance for each specimen, unlike external controls that can detect only systematic errors.

Sample Enrichment/Preparation System

The system is equipped with two magnetic separators each consisting of a set of four rectangular rare earth magnets arranged in a quadrupole configuration with a 17 mm diameter cavity surrounded by a circular steel yoke. In the present system, each separator can hold a 15 ml conical tube. In other system arrangements, different tubes may be used with different separators. Adjacent to each separator is a magnetic yoke that holds the analysis chamber (U.S. Pat. No. 6,861, 259; U.S. patent application Ser. No. 10/988,057; U.S. patent application Ser. No. 10/303,309) into which the final sample is transferred. This chamber assembly can be removed from the system and placed onto the microscope stage.

A semi-automated system was developed that immunomagnetically separates epithelial cells from 7.5 ml of blood, concurrently reduces the specimen volume and labels the cells immunofluorescently (WO 05028663). The system produces a 320 l liquid sample that is transferred to an analysis chamber and a magnetic device that causes all magnetically labeled cells in the sample to be pulled to the upper inside surface of the chamber for analysis. Four-color fluorescent analysis is performed on the sample by the CellSpotter CELLSPOTTER system that enumerates internal control cells and identifies objects that potentially classify as tumor cells by their positive staining of the nucleus, cytoplasmic cytokeratin and their lack of cell surface staining for CD45. Thumbnails of all objects that potentially classify as tumor cells are presented in the user interface from which the user can make the ultimate judgment.

Sample preparation performed by the system provides advantages when compared to the manual preparation of blood samples as demonstrated by a higher recovery and better reproducibility of enumerated tumor cells. Data from spiking experiments demonstrated an excellent linearity and sensitivity of the system. To demonstrate reproducibility of the system duplicate blood samples from 99 normal donors were processed at six different sites. Data across all sites demonstrated a level of reproducibility as assessed by recovery of internal control cells. The average recovery of the internal control was 77.1% with a coefficient of variation that varied between 3.2% and 11.8% (mean 9.7%). The sensitivity of the system was determined by the ability to detect CTC in patient samples and the specificity by identification of CTC in blood of normal donors. The analysis software identified between 10 and 304 (mean 55) candidate events in 192 normal blood samples and review of these candidates showed an average of 0.4 events that classified as CTC. In 22 patients treated for metastatic breast cancer 16 to 703 (mean 116) candidate CTC were found and 0-59 (mean 7) classified as CTC. In the blood of 15 out of 22 patients the number of CTC exceeded the upper limit of the 99% confidence interval for the average CTC count in normal individuals (mean+ 2.6*SE=0.56). In one normal blood sample, 13 events were classified as CTC by the operator, but review of the data revealed that this could be attributed to internal control cells that were weakly stained with the DiOC16. To avoid potential false positive results due to misclassification of control cells, addition of the internal control cells will only be done to demonstrate system and operator proficiency before running actual patient samples. The consistent and reproducible results between systems and operators in sample preparation and CTC analysis offers the opportunity to perform controlled clinical studies for elucidating the role of CTC levels in management of patients with carcinomas.

EXAMPLE 2

Circulating Endothelial Cell Assay

An endothelial cell capture assay using CD146 ferrofluid was utilized to detected circulating endothelial cells (FIG. 1).

The endothelial cell detection incorporated DAPI (nuclear stain), CD146 PE, and CD45 APC (non leukocyte assessment). Immunomagnetic enrichment of 4 ml blood with the AutoPrep AUTOPREP system, an immunomagnetic cell enrichment system, resulted in an enriched fraction that was subsequently analyzed on CELLSPOTTER imaging system. The results are shown in FIG. 1. Endothelial cells in healthy donors showed 2 to 47 endothelial cells per 4 ml of blood (mean 17, n=12).

EXAMPLE 3

Survey of the Frequency of CEC in Peripherial Blood

Figure 2:
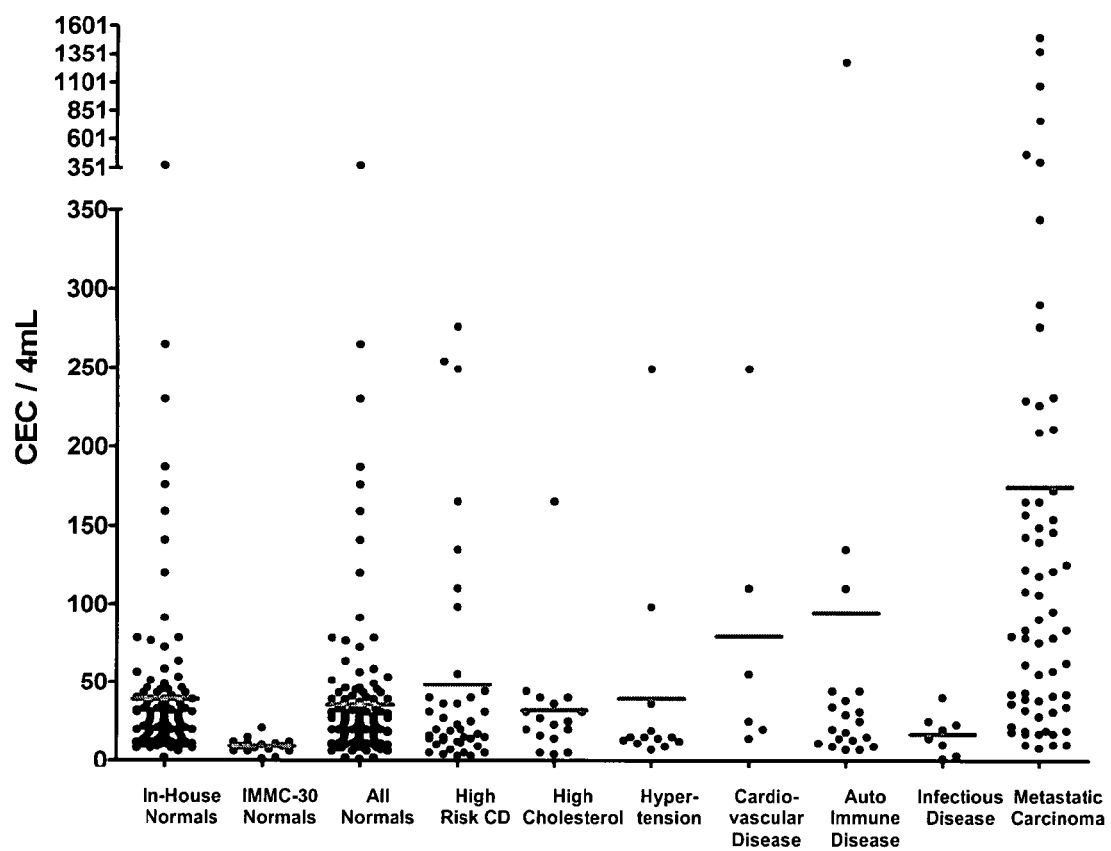
FIG. 2: Profile of circulating endothelial cells in individuals with disease compared to normal.

The integrity of the vascular endothelium is compromised by a variety of diseases and trauma, which may result in the release of luminal endothelial cells into the circulation. The isolation and enumeration of these circulating endothelial cells (CECs) provides insights into the nature of specific disease processes. Unfortunately, the frequency of CECs is low and current assay methods are laborious, complex and frequently lead to highly variable results. Hence, automation provides more consistent analytical results for clinical interpretation. The data in the present example are generated by such an automated system. To prevent degradation of endothelial cells, 4 mL of blood was drawn in CellSave Preservative Tubes. The blood was centrifuged and placed in the CELLTRACKS AUTOPREP System, an immunomagnetic cell enrichment system. This system immunomagnetically enriches cells expressing CD146 and immunofluorescently stains the enriched cells with the nucleic acid dye DAPI, endoglin (CD105)-PE and the pan-leukocyte marker CD45-APC. The sample is reduced to around 300 uL and placed in an analysis chamber that is mounted inside a magnetic "nest" to magnetically monolayer the cells. The sample is then analyzed by a semi-automated fluorescence microscope. Image analysis software detects nucleated objects with the CD105+, CD45− phenotype and the user verifies the presence of CECs among the selected objects. System accuracy and precision were validated by spiking human umbilical vein cells (HUVEC) into whole blood. In this system, 80% of 3000 pre-stained HUVEC cells spiked into 4 mL of normal blood were recovered. As shown in FIG. 2, endothelial cells were enumerated in 140 blood samples from apparently healthy donors (n=79), patients with high cholesterol and/or hypertension (n=40), autoimmune disease (n=20) or metastatic carcinoma (n=64). The mean of the CECs of the normal population plus 1 SD was used as a threshold to define the subset of individuals in each category with elevated CECs. Table 1 shows statistical comparisons with normals and the selected disease states.

TABLE 1

| CEC/4 mL | N | Average | Median | Minimum | Maximum | StdDev | Variance | % CV |
|---|---|---|---|---|---|---|---|---|
| In-House Normals | 124 | 39 | 25 | 2 | 373 | 51 | 2583 | 130% |
| IMMC-30 Normals | 16 | 9 | 9 | 1 | 21 | 5 | 23 | 53% |
| All Normals | 140 | 36 | 23 | 1 | 373 | 49 | 2380 | 137% |
| High Risk CD | 40 | 48 | 20 | 3 | 276 | 71 | 5003 | 147% |
| Hypertension | 13 | 39 | 15 | 7 | 249 | 67 | 4538 | 171% |
| High Cholesterol | 17 | 32 | 25 | 4 | 165 | 36 | 1328 | 113% |
| Cardiovascular Disease | 6 | 79 | 40 | 14 | 249 | 91 | 8212 | 115% |
| AutoImmune Diseases | 20 | 94 | 23 | 7 | 1273 | 279 | 78084 | 296% |
| Infectious Diseases | 8 | 17 | 17 | 1 | 40 | 13 | 164 | 75% |
| Metastatic Carcinomas | 64 | 175 | 83 | 8 | 1499 | 287 | 82635 | 165% |

Further phenotyping of CECs and expanded clinical information are needed to determine why elevated CECs are observed in certain apparently normal donors. However, the number of CECs was significantly increased in patients with metastatic carcinoma as compared to the other groups. The automated CELLTRACKS AUTOPREP System, an immunomagnetic cell enrichment system, is a viable means of enumerating CECs and will be used to investigate further the role of CECs in the pathogenesis of cancer and other diseases.

EXAMPLE 4

Comparison of Endothelial Cells in Peripheral Blood of Healthy vs Metastatic Carcinoma Patients To determine accuracy, precision, and linearity of an assay for the isolation and enumeration of circulating endothelial cells (CECs) and then to compare CEC counts in healthy subjects, patients with non-malignant disease and metastatic carcinoma patients.

An automated rare cell analysis system was used to enumerate nucleated, CD146+/CD105+/CD45− CECs in 4 mL of blood. A model system using blood spiked with Human Umbilical Vein Endothelial Cells (HUVECs) was used to establish assay performance. CEC levels were then measured in 249 healthy donors and 206 metastatic carcinoma patients.

Recoveries of spiked HUVECs were linear over a range of 0-1241 cells ($R2 \geq 0.99$) with recoveries of $\geq 70\%$ at each spike level. Correlation coefficient values for inter-operator variability and tube-tube variation were ($R2=0.99$ and $0.90$), respectively. Correlation of CEC counts between tubes 1-2 and 2-3 drawn from the same subject in sequence were lower (R2=0.48 and 0.63, respectively). 249 healthy individuals had 0 to 916 CECs/4 mL (mean=21±18, median=15). CEC counts were significantly higher in the 206 metastatic carcinoma patients, ranging from 0 to 1939 (mean=111±255, median=34) (P<0.0001).

Figure 3:
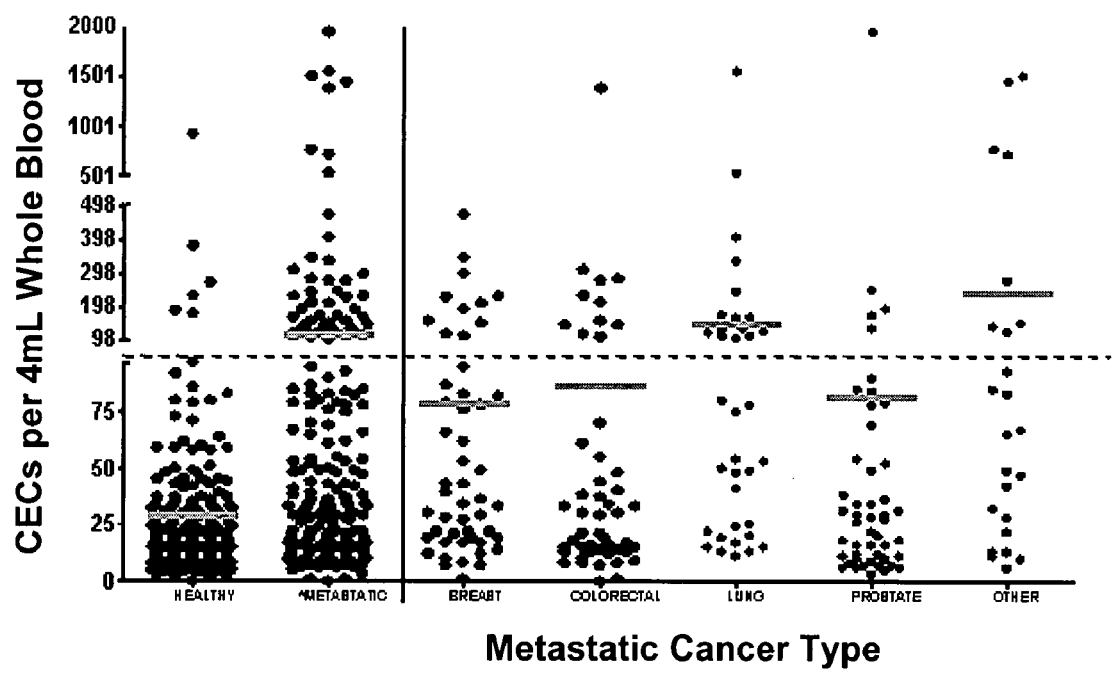
FIG. 3: Profile of circulating endothelial cells in individuals with advanced metastatic carcinoma compared to normal.

Using an automated system, CECs can be accurately and reproducibly enumerated in blood. Phlebotomy procedures may cause endothelial cell contamination of specimens. CECs are significantly elevated in a variety of metastatic carcinomas compared to healthy donors (FIG. 3).

What is claimed is:

1. A method for assessing changes in cardiovascular homeostasis, comprising:
    a. obtaining a whole blood from a test subject suspected of having a cardiovascular disorder, said whole blood specimen comprising a mixed cell population suspected of having target cells selected from the group consisting of endothelial cells, epithelial cells, and combinations thereof;
    b. contacting said whole blood specimen with a preservative capable of stabilizing said mixed population;
    c. mixing said whole blood specimen from step b with colloidal magnetic particles between 90 to 150 nm in size coated with stabilizing material and adapted to permit less than 0.3% non-specific binding and coupled to a monoclonal antibody which binds specifically to said target cells so as to capture the target cells, to the substantial exclusion of non-target cells;
    d. subjecting the specimen-magnetic particle mixture to a high gradient magnetic field to produce a separated cell fraction enriched in magnetic particle-bound target cells; and
    e. enumerating the target cells that are nucleated, CD146 positive, CD105 positive, and CD45 negative using multiparameter image cytometry wherein a change in the number of said target cells in comparison to predetermined normal control values from subjects having normal cardiovascular homeostasis provides indication of a change in cardiovascular homeostasis.

2. The method of claim 1, wherein said preservative contains an anti-coagulating agent and a stabilizing agent.

3. The method of claim 1, wherein said monoclonal antibody specifically binds cell surface antigens selected from the group consisting of CD146, CD105, and combinations thereof.

4. The method of claim 1, wherein said enumerating is indicative of changes in stenosis, organ transplant status, heart disease, or combinations thereof.

5. The method of claim 1, wherein said target cells are determined to be nucleated using a nuclear stain.

6. The method of claim 5, wherein the nuclear stain is DAPI.

* * * * *